United States Patent

Chabardes et al.

[11] Patent Number: 4,665,244
[45] Date of Patent: May 12, 1987

[54] CHLORINATED DERIVATIVES OF HEXADECENE, THEIR PREPARATION AND THEIR USE IN THE SYNTHESIS OF VITAMIN E

[75] Inventors: Pierre Chabardes, Sainte Foy Les Lyon; Michel Mulhauser, Ecully, both of France

[73] Assignee: Rhone-Poulenc Sante, Courbevoie, France

[21] Appl. No.: 777,847

[22] Filed: Sep. 19, 1985

[30] Foreign Application Priority Data

Sep. 20, 1984 [FR] France .................................. 84 14426
Mar. 15, 1985 [FR] France .................................. 85 03842

[51] Int. Cl.$^4$ ............................................. C07C 21/04
[52] U.S. Cl. .................................................... 570/189
[58] Field of Search ......................................... 570/189

[56] References Cited

U.S. PATENT DOCUMENTS 4,168,271 9/1979 Cardenas et al. .................... 549/408

Primary Examiner—Natalie Trousof
Assistant Examiner—Joseph A. Boska
Attorney, Agent, or Firm—Stevens, Davis, Miller & Mosher

[57] ABSTRACT

Hexadecene derivatives of the formulae:

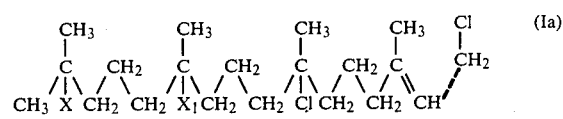

and

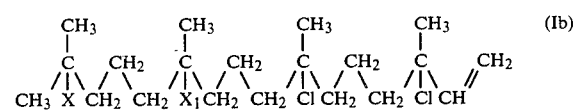

in which X and $X_1$, which may be identical or different, each represent hydrogen or chlorine, and their mixtures, are useful in the preparation of tocopherol and tocopherol acetate.

6 Claims, No Drawings

CHLORINATED DERIVATIVES OF HEXADECENE, THEIR PREPARATION AND THEIR USE IN THE SYNTHESIS OF VITAMIN E

The present invention relates to hexadecene derivatives, their preparation and their use.

The present invention provides the novel hexadecene derivatives of formula:

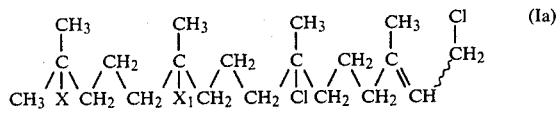

or

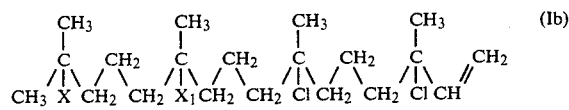

in which X and $X_1$, which can be identical or different, each represent hydrogen or chlorine.

According to a feature of the invention, the hexadecene derivatives of the formulae (Ia) and (Ib), and their mixtures, are obtained by reacting a polyene of the formula:

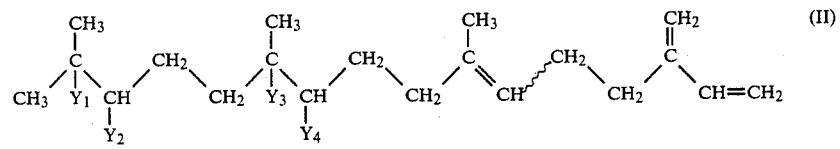

in which $Y_1$ represents hydrogen or chlorine and $Y_2$ represents hydrogen, or $Y_1$ and $Y_2$ together form a valency bond, with anhydrous hydrogen chloride gas, in the presence of a catalyst consisting of a cuprous halide, such as cuprous chloride or iodide, together with eiither a quaternary ammonium salt, e.g. a tetraalkylammonium halide or a trialkylamine hydrohalide, or a phosphonium salt, e.g. a tetraalkylphosphonium halide, in an inert organic solvent, e.g. a halogenated aliphatic hydrocarbon (for example, methylene chloride), a carboxylic acid (for example, acetic acid), a carboxylic acid anhydride (for example, acetic anhydride), an aliphatic hydrocarbon (for example, hexane), a cycloaliphatic hydrocarbon (for example, cyclohexane) or an aromatic hydrocarbon (for example, benzene). at a temperature below 20° C. and preferably below 0° C., the proportion of hydrogen chloride used being (i) if $Y_1$ represents hydrogen or chlorine and $Y_2$, $Y_3$ and $Y_4$ each represent hydrogen, at least 2 moles of anhydrous hydrogen chloride per mole of compound of formula (II); (ii) if $Y_1$ represents hydrogen or chlorine, $Y_2$ represents hydrogen, and $Y_3$ and $Y_4$ together form a valency bond, or if $Y_1$ and $Y_2$ together form a valency bond and $Y_3$ and $Y_4$ each represent hydrogen, at least 3 moles of anhydrous hydrogen chloride per mole of compound of the formula (II); or (iii) if $Y_1$ and $Y_2$ and $Y_3$ and $Y_4$ respectively together form a valency bond, at least four moles of anhydrous hydrogen chloride per mole of compound of formula (II).

The compounds of formula (II) in which $Y_3$ and $Y_4$ each represent hydrogen and $Y_1$ and $Y_2$ each represent hydrogen or together form a valency bond can be obtained under the conditions described in U.S. Pat. No. 4,292,495.

The compound of formula (II) in which $Y_1$ represents a chlorine atom, $Y_2$ represents a hydrogen atom and $Y_3$ and $Y_4$ together form a valency bond can be obtained from myrcene by condensing the magnesium derivative of 1,7-dichloro-3,7-dimethyl-octene with 3-chloro-myrcene. 1,7-Dichloro-3,7-dimethyl-octene can be obtained by reacting myrcene with at least two moles of anhydrous hydrogen chloride per mole of myrcene in the presence of a catalyst consisting of a cuprous halide, such as cuprous chloride or iodide, together with (a) a quaternary ammonium salt, such as a tetraalkylammonium halide or a trialkylamine hydrohalide, or (b) a phosphonium salt such as a tetraalkylphosphonium halide, in an inert organic solvent which may be a halogenated aliphatic hydrocarbon (e.g. methylene chloride), a carboxylic acid (e.g. acetic acid), a carboxylic acid anhydride (e.g. acetic anhydride), an aliphatic hydrocarbon (e.g. hexane), a cycloaliphatic hydrocarbon (e.g. cyclohexane) or an aromatic hydrocarbon (e.g. benzene), at a temperature below 20° C., and preferably below 0° C.

The magnesium derivative of 1,7-dichloro-3,7-dimethyl-octene is obtained under the usual conditions by reaction of 1,7-dichloro-3,7-dimethyl-octene with magnesium, in an organic solvent chosen from the ethers (e.g. ethyl ether or tetrahydrofuran), at a temperature below 0° C.

The condensation of the magnesium compound of 1,7-dichloro-3,7-dimethyl-octene with 3-chloro-myrcene is generally carried out at a temperature below 0° C. in an organic solvent chosen from the ethers (e.g. ethyl ether or tetrahydrofuran) in the presence of a cuprous halide such as cuprous iodide.

The product of the general formula (II) in which $Y_1$ and $Y_2$ and $Y_3$ and $Y_4$ respectively form a valency bond, that is to say β-springene, can be obtained by reaction of the magnesium derivative of geranyl and neryl chlorides with 3-chloro-myrcene.

The mixture of geranyl and neryl chlorides can be obtained by hydrochlorination of myrcene in the presence of one mole of anhydrous hydrogen chloride per mole of myrcene under the conditions described above for the preparation of 1,7-dichloro-3,7-dimethyl-octene.

The magnesium derivative of the mixture of geranyl chloride and neryl chloride can be obtained under the conditions described above for the preparation of the magnesium derivative of 1,7-dichloro-3,7-dimethyl-octene.

The products of formula (Ia) and (Ib) obtained according to the process of the present invention are particularly useful in the synthesis of vitamin E.

For example, a product of formula (Ia) or (Ib) can be condensed with trimethylhydroquinone to give the product of the formula

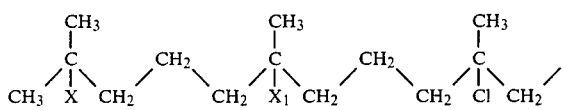 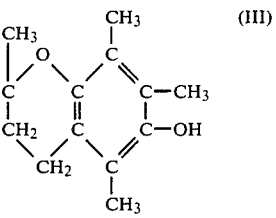

in which the symbols X and $X_1$ are defined as above, and this can be hydrogenated to give tocopherol or, after acetylation, tocopherol acetate.

In general the condensation of the product of the formula (Ia) or (Ib) with trimethylhydroquinone is carried out in the presence of zinc chloride in an organic solvent chosen from acetic acid and dioxane at a temperature between 0° and 50° C.

The acetylation of a product of the formula (III) is generally carried out with acetic anhydride in the presence of zinc chloride or in the presence of a mixture of triethylamine and dimethylaminopyridine at a temperature of about 20° C.

The hydrogenation of the product of the general formula (III) or of its acetate to give tocopherol or tocopherol acetate can be carried out with hydrogen in the presence of a catalyst such as palladium on charcoal, in an organic solvent such as acetic acid or ethanol, at a temperature of between 50° and 100° C., where appropriate under pressure.

The Examples which follow show how the invention can be put into practice.

EXAMPLE 1

Triethylamine hydrochloride (3.4 g), cuprous chloride (2.5 g) and methylene chloride (270 cc) are introduced under an argon atmosphere into a 500 cc three-neck flask equipped with a magnetic stirrer, a thermometer and a dip tube. The mixture is cooled to $-10°$ C. and to the yellow homogeneous solution thus obtained there is added myrcene (136 g=1 mole), of purity greater than 95%, followed, over the course of 6 hours, by anhydrous hydrogen chloride (80 g). The solution thus obtained is kept at $-25°$ C. for 18 hours.

The reaction mixture is poured into a mixture of an aqueous 10% strength ammonium chloride (400 cc) and pentane (300 cc). After phase separation, the organic phase is washed with water (3×200 cc) and is then dried over potassium carbonate. After filtration and evaporation of the solvent, a pale yellow oil (237.8 g) is obtained, which essentially contains 1,7-dichloro-3,7-dimethyl-oct-2-ene in the form of a mixture of the E and Z isomers.

Magnesium (12.15 g), tetrahydrofuran (30 cc) and one crystal of iodine are introduced into a 250 cc reactor. The mixture is cooled to $-20°$ C. and a solution of the 1,7-dichloro-3,7-dimethyl-oct-2-ene (20.9 g) obtained above, in tetrahydrofuran (85 cc) is added over the course of 5 hours 30 minutes. Stirring is continued for 18 hours at $-20°$ C. The excess magnesium is removed by filtration and the solution obtained is introduced into a dropping funnel, with exclusion of air and moisture.

Copper iodide (0.5 g) and tetrahydrofuran (5 cc) are introduced into a 250 cc reactor and the solution of the magnesium compound (1.5 cc) is added. Thereafter 3-chloromyrcene (19.5 g), of purity greater than 87%, in tetrahydrofuran (10 cc) is added rapidly. The mixture is cooled to $-20°$ C. and the remaining solution of the magnesium compound is added over the course of 3 hours. The temperature is allowed to return to about 20° C. over the course of 1 hour. Water (5 cc) and pentane (100 cc) are added to the reaction mixture. The organic phase is decanted off and dried over magnesum sulphate. After filtration and evaporation of the solvent, an oil (29.7 g) is obtained.

According to vapour phase chromatographic determination with an internal standard, the degree of conversion of the 3-chloro-myrcene is 69%.

The oil obtained is heated to 100°–105° C. under reduced pressure (0.5–1 mm Hg; 0.067–0.13 kPa) to remove the unreacted $C_{10}$ products.

The residue obtained (20 g) contains 85% of 15-chloro-3-methylene-7,11,15-trimethyl-hexadeca-1,6,10-triene.

The yield is 82% relative to the 3-chloro-myrcene consumed.

The structure of the product obtained is confirmed by the mass spectrum and the proton nuclear magnetic resonance spectrum.

Triethylamine hydrochloride (0.48 g), methylene chloride (15 cc), acetic acid (10 cc) and cuprous chloride (90 mg) are introduced, under an argon atmosphere, into a 250 cc reactor. The reaction mixture is stirred until a homogeneous solution is obtained. This is cooled to $-10°$ C. and 15-chloro-3-methylene-7,11,15-trimethyl-hexadeca-1,6,10-triene (10 g) is then added followed, over the course of 1 hour, by dry gaseous hydrogen chloride (3.9 g). The reaction mixture is poured into an aqueous solution (100 cc) of ammonium chloride (100 g/liter). The organic phase is removed by decanting and the aqueous phase is then extracted with methylene chloride (twice 100 cc). The combined organic phases are washed with water (100 cc) and then dried over potassium carbonate. After filtration and evaporation of the solvent, 1,7,11,15-tetrachloro-3,7,11,15-tetramethyl-hexadec-2-ene (13.1 g) is obtained in a yield of 96.5%.

The structure of the product obtained is confirmed by the mass spectrum.

EXAMPLE 2

Triethylamine hydrochloride (0.48 g), methylene chloride (15 cc), acetic acid (10 cc) and cuprous chloride (90 mg) are introduced, under an argon atmosphere, into a 250 cc reactor. The reaction mixture is stirred until a homogeneous solution is obtained. This is cooled to $-10°$ C. and β-springene (10 g) is then added, followed, over the course of 1 hour, by dry hydrogen chloride gas (5.2 g). After treatment of the reaction mixture under the conditions described above, 1,7,11,15-tetrachloro-3,7,11,15-tetra-methylhexadec-2-ene (14.2 g) is obtained in a yield of 94%.

The structure of the product obtained is confirmed by its hydrogenation to phytane.

EXAMPLE 3

Trimethylhydroquinone (8.4 g), 1,7,11,15-tetrachloro-3,7,11,15-tetramethyl-hexadec-2-ene (22 g) and acetic acid (30 cc) are introduced into a 250 cc reactor. A solution of zinc chloride (1.5 g) in anhydrous acetic acid (15 cc) is then added over the course of 10 minutes. The temperature rises from 25° to 30° C. The reaction mixture is stirred for 2 hours at 30° C. and is then poured into a mixture of hexane (100 cc) and water (100 cc). The organic phase is removed by decanting, and washed with a mixture (100 cc) of methanol and water (50:50 by volume). A white precipitate forms in the hexane phase; it is filtered off and washed with a mixture (50 cc) of methanol and water (50:50 by volume). After drying under reduced pressure, 2,5,7,8-tetramethyl-2-(4',8',12'-trichloro-4',8',12'-tri-methyl-tridecyl)-chroman-6-ol (14.3 g) is obtained in the form of white crystals melting at 102°–104° C. The yield is 62%.

The structure of the product is confirmed by the mass spectrum and the proton nuclear magnetic resonance and $^{13}$C nuclear magnetic resonance spectra.

EXAMPLE 4

Fused zinc chloride (0.22 g), trimethylhydroquinone (2.47 g) and anhydrous dioxane (10 cc) are introduced into a 250 cc reactor. The mixture is heated to 40°–45° C. and a solution of 1,7,11,15-tetrachloro-3,7,11,15-tetramethylhexadec-2-ene (6.8 g) in dioxane (7 cc) is then added over the course of 20 minutes. Stirring is continued for 1 hour 30 minutes. This reaction mixture is poured into an aqueous solution (50 cc) of ammonium chloride (100 g/liter). The mixture is extracted with ethyl acetate (twice 50 cc) and the organic phases are then dried over magnesium sulphate. After filtration and evaporation of the solvent, 2,5,7,8-tetramethyl-2-(4',8',12'-trichloro-4',8',12'-trimethyltridecyl)-chroman-6-ol is obtained in a yield of 43.5%.

EXAMPLE 5

The product obtained in Example 3 (2.1 g), dimethylaminopyridine (150 mg) and triethylamine (10 cc) are introduced, under an argon atmosphere, into a three-neck flask and acetic anhydride (6 cc) is then added rapidly, with stirring, at a temperature of 25° C. After 1 hour's stirring, water (20 cc) is added and the reaction mixture is thereafter neutralised by gradual addition of sodium carbonate until the evolution of carbon dioxide gas ceases. The reaction mixture is extracted with ethyl acetate (twice 50 cc). The organic phase is washed with a 0.1N aqueous hydrochloric acid solution (3 times 50 cc). The organic phases are dried over magnesium sulphate. After filtration and evaporation of the solvent, the residue obtained is taken up in hexane. The precipitate which forms is filtered off. This gives a 93% yield of 2,5,7,8-tetramethyl-2-(4',8',12'-trichloro-4',8',12'-trimethyl-tridecyl)-chroman-6-ol acetate, melting at 95°–105° C.

The structure of the product is confirmed by mass spectrum and the proton nuclear magnetic resonance and $^{13}$C nuclear magnetic resonance spectra.

EXAMPLE 6

The product obtained in Example 3 (5 g), acetic acid (20 cc) and anhydrous zinc chloride (320 mg) are introduced, under an argon atmosphere, into a reactor. A solution (5 cc) of hydrochloric acid in acetic acid (1.9 moles of hydrochloric acid per liter) is added. Thereafter, acetic anhydride (2.7 cc) is added over 15 minutes. The temperature rises from 20° to 30° C. After 2 hours' stirring, water (10 cc), sodium acetate (800 mg) and ethyl acetate (100 cc) are added. After evaporation of the solvents, the residue is taken up in methylene chloride. After filtration over silica gel, 2,5,7,8-tetramethyl-2-(4',8',12'-trichloro-4',8',12'-trimethyl-tridecyl)-chroman-6-ol acetate (4.99 g) is obtained.

The degree of conversion of the 2,5,7,8-tetramethyl-2-(4',8',12'-trichloro-4',8',12'-trimethyl-tridecyl)-chroman-6-ol is 100%. The yield is 92.5%.

EXAMPLE 7

Zinc chloride (186 mg) and acetic acid (3 cc) are introduced, under an argon atmosphere, into a reactor. Trimethylhydroquinone (1.85 g), acetic acid (1.5 cc) and methylene chloride (4.5 cc) are then added. Thereafter the product obtained in Example 3 (5.1 g), dissolved in acetic acid (4 cc) and methylene chloride (4 cc) is added over 15 minutes, at 23° C. After 2 hours' stirring at a temperature of between 22° and 25° C., acetic anhydride (3.5 cc) is added. The temperature rises to 32° C. After 15 hours at a temperature of about 25° C., water (100 cc) is added, followed by sodium bicarbonate until the mixture is neutral. The mixture is extracted with ethyl acetate (twice 50 cc). The organic phases are dried over potassium carbonate. After filtration and evaporation of the solvent, an oil (5.82 g) containing 64% of 2,5,7,8-tetramethyl-2-(4',8',12'-trichloro-4',8',12'-trimethyl-tridecyl)-chroman-6-ol acetate is obtained.

The yield is 53%.

EXAMPLE 8

The product obtained in Example 5 (1 g), acetic acid (20 cc) and palladium on charcoal (0.1 g), containing 10% of palladium, are introduced into a three-neck flask equipped with a magnetic stirrer, a thermometer and a condenser topped by a hydrogenation head. The reaction mixture is heated to 80° C. under hydrogen at atmospheric pressure. The theoretical amount of hydrogen is absorbed in 2 hours. After cooling, the catalyst is filtered off. After evaporation of the solvent, a very pale yellow oil (0.9 g) containing 89.5% by weight of tocopherol acetate is obtained.

EXAMPLE 9

The product obtained in Example 3 (2.04 g), palladium on charcoal (44 mg) containing 10% of palladium, and ethanol (25 cc) are introduced into an autoclave. A hydrogen pressure of 50 bars is set up and the mixture is then heated at 80° C. for 5 hours, with constant stirring. After cooling, removal of the catalyst by filtration, and evaporation of the solvent, tocopherol is obtained in a yield of 96%.

EXAMPLE 10

Triethylamine hydrochloride (360.5 mg=0.26×10$^{-2}$ mole), cuprous chloride (126 mg=0.13×10$^{-2}$ mole), acetic acid (9 cc) and methylene chloride (9 cc) are introduced, under an argon atmosphere, into a 250 cc three-neck flask. The mixture is stirred until a yellow homogeneous solution is obtained. It is cooled to 0° C. and 3-methylene-7,11,15-trimethyl-hexadeca-1,6-diene (13.96 g), of 95% purity, is then added rapidly. The solution is cooled to a temperature of about −5° C. and a stream of anhydrous hydrogen chloride gas is then introduced for 1 hour 20 minutes so as to introduce hydrogen chloride (5 g=0.137 mole). After 30 minutes' stirring at a temperature of about −5° C., the reaction mixture is poured into pentane (20 cc) and an aqueous solution (20 cc) of ammonium chloride (10% strength by weight), at a temperature of about 20° C. The organic phase is removed by decanting and then dried over sodium sulphate. After filtration and evaporation of the solvent, a crude product (17.31 g) is obtained, the analysis of which by mass spectrography and by proton nuclear magnetic resonance shows the presence of 90% of a mixture of 1,7-dichloro-3,7,11,15-tetramethyl-hexadec-2-ene and 3,7-dichloro-3,7,11,15-tetramethyl-hexadec-1-ene.

To confirm that the skeleton of the product obtained is linear, some of the product obtained above (1.7 g), dissolved in ethanol (20 cc) is treated with hydrogen under a pressure of 20 bars at 80° C. in the presence of 10% strength palladium on charcoal (170 mg). After filtering off the catalyst and evaporating the solvent, vapour phase chromatographic determination with an internal standard shows that the yield of phytane is 83.7% relative to the triene employed.

The selectivity in respect of phytane relative to the other isomers is 98%.

EXAMPLE 11

Anhydrous zinc chloride (990 mg=0.007 mole) dissolved in acetic acid (20 cc) is introduced, under an argon atmosphere, into a 250 cc three-neck flask. Trimethylhydroquinone (4.4 g=0.0289 mole) is then added. Onto this heterogeneous mixture is poured, over the course of 40 minutes at a temperature of between 20° and 26° C., the product obtained in Example 10 (10 g) dissolved in acetic acid (20 cc). The mixture becomes homogeneous and has a brownish red colour. After 1 hour's stirring, acetic anhydride (10 cc) is added and stirring is then continued for a further 2 hours. After hydrolysis with water, extraction with ether and drying over magnesium sulphate, the solvent is evaporated under reduced pressure. This gives a yellow oil (16.2 g), the analysis of which by mass spectrometry, proton nuclear magnetic resonance and $^{13}C$ nuclear magnetic resonance shows that it essentially consists of 2,5,7,8-tetramethyl-2-(4',-chloro-4',8'12'-trimethyl-tridecyl)-chroman-6-ol acetate.

The degree of conversion (determined by measuring the trimethylhydroquinone diacetate recovered) is 80.4%.

EXAMPLE 12

The product (6.67 g) obtained in Example 11, acetic acid (60 cc) and palladium on charcoal (400 mg) containing 10% by weight of palladium are introduced into a hydrogenation apparatus. The mixture is heated at 80° C. for 2 hours 30 minutes under a hydrogen pressure of 1 bar. After cooling, filtering off the catalyst and evaporating the solvent, a clear oil (5.62 g) containing 74.7% of tocopherol acetate is obtained.

The yield of tocopherol acetate is 93% relative to the trimethylhydroquinone which has reacted, and 80% relative to the 3-methylene-7,11,15-trimethyl-hexadeca-1,6-diene which has reacted.

The degree of conversion of the 1,7-dichloro-3,7,11,15-tetramethyl-hexadec-2-ene and 3,7-dichloro-3,7,11,15-tetramethyl-hexadec-1-ene is 97%, the determination being carried out by measuring the phytane recovered.

EXAMPLE 13

The procedure of Example 10 is employed, but starting from the following products:

| | |
|---|---|
| 2-methylene-7,11,15-trimethyl-hexadeca-1,6,14-triene | 14 g (5.1 × $10^{-2}$ mole) |
| triethylamine hydrochloride | 370 mg |
| cuprous chloride | 130 mg |
| acetic acid | 9 cc |
| methylene chloride | 9 cc |

A stream of anhydrous hydrogen chloride gas is passed through the mixture for 1 hour so as to introduce hydrogen chloride (7.3 g).

After treatment of the reaction mixture, an oil (19.31 g) is obtained, the analysis of which by mass spectrometry and proton nuclear magnetic resonance shows that it essentially consists of 1,7,15-trichloro-3,7,11,15-tetramethyl-hexadec-2-ene and 3,7,15-trichloro-3,7,11,15-tetramethyl-hexadec-1-ene and that it does not contain conjugated dienes.

The hydrogenation of the product obtained, under the conditions described in Example 1, shows that according to vapour phase chromatographic determination with an internal standard, the yield of phytane is 63% relative to the 2-methylene-7,11,15-trimethyl-hexadeca-1,6,14-triene employed.

EXAMPLE 14

The procedure of Example 11 is employed, but starting from the following products:

| | |
|---|---|
| product of Example 4 | 10 g |
| trimethylhydroquinone | 4 g |
| zinc chloride | 914 mg |
| acetic acid | 43 cc |
| acetic anhydride | 10 cc |

After treatment of the reaction mixture, an orange oil (16.63 g) is obtained.

The degree of conversion of the trimethylhydroquinone is 81.3% (as determined by measuring the trimethylhydroquinone diacetate).

The structure of the 2,5,7,8-tetramethyl-2-(4',12'-dichloro-4',8',12'-trimethyl-tridecyl)-chroman-6-ol acetate is confirmed by the mass spectrum and the proton nuclear magnetic resonance and $^{13}C$ nuclear magnetic resonance spectra, measured on a purified fraction of the oil obtained.

EXAMPLE 15

The oil (2.9 g) obtained in Example 14 is dissolved in acetic acid (30 cc) containing palladium on charcoal (220 mg), itself containing 10% by weight of palladium. The mixture is heated at 80° C. for 4 hours 30 minutes under a hydrogen pressure of 1 bar. After treatment of the reaction mixture a clear oil (2.17 g) containing 62% of tocopherol acetate is obtained.

The yield of tocopherol acetate is 76.7% relative to the trimethylhydroquinone which has reacted and 65% relative to the 2-methylene-7,11,15-trimethyl-hexadeca-1,6,14-triene which has reacted.

The degree of conversion of the 1,7,15-trichloro-3,7,11,15-tetramethyl-hexadec-2-ene and 3,7,15-trichloro-3,7,11,15-tetramethyl-hexadec-1-ene is 97%, the determination being carried out by measuring the phytane recovered.

We claim:

1. A hexadecene derivative of the formula:

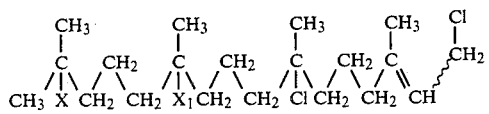

or

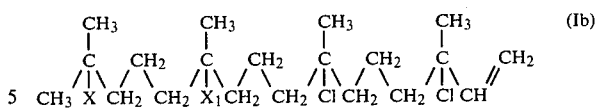

and mixtures thereof, in which X and $X_1$, which may be identical or different, each represent hydrogen or chloride, and the wavy line ⁓⁓⁓ indicates that the terminal $CH_2$ radical of Formula (1a) is in the cis- or trans-configuration.

2. The compound according to claim 1 which is 1,7,11,15-tetrachloro-3,7,11,15-tetramethyl-hexadec-2-ene.

3. The compound according to claim 1 which is 1,7-dichloro-3,7,11,15-tetramethyl-hexadec-2-ene.

4. The compound according to claim 1 which is 3,7-dichloro-3,7,11,15-tetramethyl-hexadec-1-ene.

5. The compound according to claim 1 which is 1,7,15-trichloro-3,7,11,15-tetramethyl-hexadec-2-ene.

6. The compound according to claim 1 which is 3,7,15-trichloro-3,7,11,15-tetramethyl-hexadec-1-ene.

* * * * *